(12) United States Patent
Heinemann et al.

(10) Patent No.: US 8,916,690 B2
(45) Date of Patent: Dec. 23, 2014

(54) GROWTH-INHIBITED HYDROXYAPATITE, PROCESS FOR ITS PREPARATION AND USE

(75) Inventors: Sascha Heinemann, Dresden (DE); Christiane Heinemann, Dresden (DE); Hartmut Worch, Dresden (DE); Thomas Hanke, Berlin (DE); Wolfgang Pompe, Hartha (DE)

(73) Assignee: Technische Universität Dresden, Dresden (DE)

( * ) Notice: Subject to any disclaimer, the term of this patent is extended or adjusted under 35 U.S.C. 154(b) by 0 days.

(21) Appl. No.: 13/812,497

(22) PCT Filed: Aug. 4, 2011

(86) PCT No.: PCT/EP2011/063470
§ 371 (c)(1),
(2), (4) Date: Jan. 26, 2013

(87) PCT Pub. No.: WO2012/017045
PCT Pub. Date: Feb. 9, 2012

(65) Prior Publication Data
US 2013/0122067 A1 May 16, 2013

(30) Foreign Application Priority Data
Aug. 4, 2010 (DE) .......................... 10 2010 038 926

(51) Int. Cl.
| | | |
|---|---|---|
| C08H 1/00 | (2006.01) | |
| A61L 27/44 | (2006.01) | |
| A61L 27/48 | (2006.01) | |
| A61L 27/12 | (2006.01) | |
| C01B 25/32 | (2006.01) | |
| A61F 2/28 | (2006.01) | |
| A61L 27/46 | (2006.01) | |
| A61L 27/24 | (2006.01) | |

(52) U.S. Cl.
CPC ................. *A61F 2/28* (2013.01); *A61L 27/446* (2013.01); *A61L 27/48* (2013.01); *A61L 27/12* (2013.01); *C01B 25/32* (2013.01); *A61L 27/46* (2013.01); *A61L 27/24* (2013.01)
USPC .......................................... 530/402; 530/356

(58) Field of Classification Search
USPC .................................................. 530/356, 402
See application file for complete search history.

(56) References Cited

U.S. PATENT DOCUMENTS

| | | | |
|---|---|---|---|
| 6,384,197 B1 * | 5/2002 | Weis et al. ..................... | 530/356 |
| 2009/0155320 A1 | 6/2009 | Rudin et al. | |
| 2009/0232875 A1 | 9/2009 | Tampieri et al. | |

FOREIGN PATENT DOCUMENTS

DE    10 2004 058 893 A1    6/2006

OTHER PUBLICATIONS

Hao et al., Temporal and Spatial Localization of the Dentin Matrix Proteins During Dentin Biomeneralization, Mar. 1, 2009, Journal of HIstochemistry and Cytochemistry, vol. 57 iss. 3, pp. 227-237.*
Bradt J. H. et al.: "Biomimetic Mineralization of Collagen by Combined Fibril Assembly and Calcium Phosphate Formation"; Chemistry of Materials, vol. 11, No. 10, (Oct. 1, 1999) pp. 2694-2701; see international search report.
Max-Planck-Forschung, Ed.: Knochen auf den Zahn gefühlt; vol. 1, 2005, pp. 10-11; discussed in instant specification, p. 1, last paragraph.
Tadic D. et al.: A thorough physicochemical characterisation of 14 calcium phosphate-based bone substitution materials in comparison to natural bone; Biomaterials 25 (2004) 987-994; discussed in instant specification, p. 3, first paragraph.
Murugan R. et al.: Development of nanocomposites for bone grafting; Composites Science and Technology 65 (2005) 2385-2406; discussed in instant specification, p. 3, first paragraph.
Detsch R. A. et al.: Is hydroxyapatite ceramic included in the bone remodeling process? An in vitro study of resorption and formation processes; Key Engineering Materials vols. 361-363 (2008) 1123-1126; discussed in instant specification, p. 3, first paragraph.
Müller P. et al.: Calcium phosphate surfaces promote osteogenic differentiation of mesenchymal stem cells; J. Cell. Mol. Med. vol. 12 (2008) 281-291; discussed in instant specification, p. 3, second paragraph.
Detsch R. et al.: Formation of osteoclast-like cells on HA and TCP ceramics; Acta Biomaterialia 4 (2008) 139-148; discussed in instant specification, p. 3, second paragraph.
Malafaya P. B. et al.: Bilayered chitosan-based scaffolds for osteochondral tissue engineering: Influence of hydroxyapatite on in vitro cytotoxicity and dynamic bioactivity studies in a specific double-chamber bioreactor; Acta Biomaterialia 5 (2009) 644-660; discussed in instant specification, p. 4, first paragraph.

* cited by examiner

*Primary Examiner* — Ali Soroush
(74) *Attorney, Agent, or Firm* — Gudrun E. Huckett (57) ABSTRACT

The invention relates to growth-inhibited hydroxyapatite for improving bone healing. It differs from the apatites employed to date in that it releases calcium ions and phosphate ions in physiological solutions, which, unlike traditional hydroxyapatites, it does not bind. It thereby promotes bone regeneration and bone growth. The growth-inhibited hydroxyapatite contains in agglomerates of prestructured collagen templates on which hydroxyapatite crystals with a crystallite growth of below its critical nucleus radius are formed epitactically. It is prepared by the steps a) mineralization of prestructured collagen templates in supersaturated Ca- and phosphate-ion-containing solutions, where the prestructured collagen templates are capable of diffusion and/or migration, so that HAP crystallites grow epitactically on the collagen templates and the collagen templates grown together with HAP crystallites agglomerate due to their capability of diffusion and/or migration, b) separating off the agglomerates.

4 Claims, 4 Drawing Sheets

GROWTH-INHIBITED HYDROXYAPATITE, PROCESS FOR ITS PREPARATION AND USE

BACKGROUND OF THE INVENTION

The invention concerns growth-inhibited hydroxyapatite (referred to in the following as wHAP) for the improvement of bone healing. It differs from the apatites used already up to now in that it releases calcium and phosphate ions in physiological solutions and, in contrast to customary hydroxyapatites, does not bind them. Thereby it promotes new bone formation and bone growth.

The development of new biomaterials is primarily driven by the desire to produce technically mature tissue implants and bone implants for medical applications, However, they are subject to special demands, depending on implantation site, with regard to biocompatibility, mechanical strength, degradation behavior in case of resorbable implants, and bioactivity. The term bioactivity characterizes the ability of a material to support the formation of an apatite layer (bone mineral) on the surface in the presence of natural or simulated body fluid.

The mammalian bone fulfils in the organism supporting functions as well as metabolic functions [Wintermantel, E.; Ha, S. W.: Medizintechnik—Life Science Engineering, Springer Verlag, 2008]. The bone masters the resulting varied demands by its hierarchical construction and by its material composition. The organic bone matrix which makes up approx. 30% of the bone is comprised of up to approx. 95% of collagen. In the course of a mineralization process, mineral calcium phosphate (primarily hydroxyapatite) is deposited between the collagen fibrils in the form of crystalline platelets having a thickness of about two to four nanometers [chapter Forschung aktuell. In: Max-Plank-Forschung (Ed.): Knochen auf den Zahn gefühlt; vol. 1., 2005, pages 10-1]. Depending on the degree of mineralization (in bone approx 65%) the flexible basic scaffold of collagen is strengthened mechanically causing the strength to increase enormously, primarily under pressure load. Based on such findings, for some time now possibilities for the imitation of naturally occurring composite materials, primarily of bone, have been worked on intensively.

In direct bone contact, primarily the degradation behavior decides the destiny of the interacting intravascular or tissue cells in case of resorbable biomaterials. The term degradation behavior is understood in this context as release of substances from the material into the surrounding tissue or the absorption of substances from the surroundings and deposition on the implant surface. In case of the calcium and phosphate balance, the absorption of ions from the surroundings with deposition on the implant surface in the form of an apatite layer is referred to as bioactive behavior. In the field of bone substitution materials it has been reported repeatedly that a high bioactivity can promote the formation of a force-fit connection between implant and recipient tissue. On the other hand, some publications also report negative effects on the cell behavior in connection with a high bioactivity of the biomaterial. From this it can be derived that the ion balance that is determined by the degradation behavior of the biomaterial has a determinative influence on the cell behavior, on the implant surface as well as in the tissue areas close to the implant, and thus on bone remodeling and finally on the success of the treatment.

Materials on the basis of collagen and collagen derivatives are of especially great interest for biomedical applications. As the body's own structural protein it is ubiquitous in all multicellular animals and is the most frequent protein, constituting about one third of the whole protein mass. It is nearly non-toxic, bioresorbable and hardly immunogenic, resulting in an excellent biocompatibility. As a starting material for industrial uses, collagen of the type I is mostly used which can be obtained, for example, from tendons, cartilage and skins of cattle, calves and pigs. Meanwhile numerous products on the basis of collagen have been developed and have been established in many areas of cosmetics and medicine. Gelatin, also established in numerous uses, is a denatured collagen. Since collagen-based products alone as a rule do not match the mechanical requirements as a bone substitute, they are substituted or supplemented with inorganic-non-metallic phases.

In the field of calcium phosphate-based bone substitution materials, these are primarily hydroxyapatite (HAP) and tri-calcium phosphate (TCP) as well as mixtures of both phases used [Tadic D, Epple M.; A thorough physicochemical characterization of 14 calcium phosphate-based bone substitution materials in comparison to natural bone. Biomaterials 2004; 25 (6): 987-94]. Hydroxyapatite of biological origin (e.g., the commercially available Endobon, Cerabone) or synthetic origin (e.g., Cerapatite, Ostim) applied in powder form, granular form, block-shaped or pasty form is little bioresorbable [Murugan R, Ramakrishna S., Development of nanocomposites for bone grafting. Comp Sci Tech 2005; 65 2385-406. Hydroxyapatite is considered insoluble in the neutral pH range on account of its composition, crystalline structure and mostly low microporosity. The comparably slow degradation processes in vivo are attributed almost exclusively to cellular resorption [Detsch R A, Mayr H B, Seitz D B, Ziegler G.; Is hydroxyapatite ceramic included in the bone remodeling process? An in vitro study of resorption and formation processes. Key Engineering Materials 2008; 361-363 II 1123-1126], Higher degradation rates can be reached with HAP/TCP mixtures (e.g., 4-Bone, Bonesave) or pure TCP (e.g., Biobase, Cerasorb). However, the degradation behavior of TCP is calculable only with difficulty.

The calcium phosphate phase serves in the natural bone not only for increasing the strength, but is also a calcium supplier in the course of bone metabolism or remodeling. Knowledge of how this occurs in the human organism in the healthy bone is sketchy; in which manner this process intervenes in the healing of defects when degradeable biomaterials are used, is not understood in detail yet and is the object of research. Of special interest is the healing of defects of the osteoporotic bone which occurs, as is known, more slowly. In some publications it has been demonstrated that the calcium concentration in implant surroundings that is affected by the solubility of the implant material has effects on the proliferation and differentiation behavior of stem cells, osteoblasts and osteoclasts [Muller P, Bulnheim U. Diener A, Luthen F, Teller M, Klinkenberg E D, Neumann H G, Nebe B, Liebold A, Steinhoff G, Rychly J.; Calcium phosphate surfaces promote osteogenic differentiation of mesenchymal stem cells. J Cell Mol Med 2008; 12 (1): 281-91]. As described by Detsch et al., a high calcium ion concentration, as obtained e.g. for TCP-based materials, reduces the resorption activity of osteoclasts [Detsch R, Mayr H, Ziegler G.; Formation of osteoclast-like cells on HA and TCP ceramics. Acta Biomater 2008; 4 (1): 139-48]. The most recent publication attributes cytotoxicity in vitro to unsintered hydroxyapatite in the form of a composite of chitosan and HAP, which is explained by reduced calcium or magnesium contents [Malafaya P B, Reis R L. Acta Biomater 2009; 5 644-60].

DE 10 2004 058 893 A1 discloses a method for modifying biopolymers. An example of this process is the use of fibril-forming collagen modified with chondroitin sulfate (CS), wherein upon later implantation the modified collagen reacts with a monomer, glucuronic acid, produced by the metabolic decomposition of the heterodimeric CS present at the collagen. In the course of this reaction, amino acids of the collagen, primarily the ω amino group of lysine, was carboxymethylated causing regions of the collagen surface to become negatively loaded. As a result of the carboxymethylation, calcium ions present in the vicinity are bound. In this way, a heterogeneous nucleus formation of calcium phosphate phases is initiated and the mineral formation, e.g., the biomimetic preparation of HAP in the surroundings of carboxymethylated collagen, is accelerated and intensified.

The carboxymethylated templates are mineralized according to the DCCM or DMDM method. The carboxymethylated templates are fixedly adsorbed on a surface of the employed membranes. In the presence of calcium and phosphate ions the carboxymethylated templates mineralize.

When an supersaturated electrolyte solution with Ca and $PO_4$ ions is present, nuclei of hydroxyapatite form on collagen fibril surfaces at individual selected sites and do not cover the surface evenly and grow together undefined in the course of growth. In this context, FIG. 1a and FIG. 1b show scanning electron microscope images of hydroxyapatite deposited on collagen I fibrils.

Figure 1A:
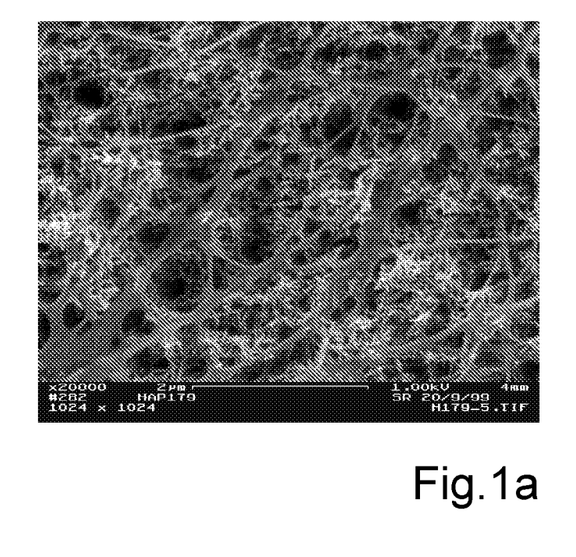
FIG. 1a TEM image growth of HAP on collagen fibrils,
FIG. 1b TEM image unhindered growth of HAP prestructured collagen template,
FIG. 2 maximum-resolution TEM—image of a prestructured collagen molecule with epitactically deposited wHAP,
FIG. 3 TEM image of spherical wHAP agglomerates,
FIG. 4 diagram solution precipitation behavior of different HAP.

FIG. 1a shows the deposition process after 15 minutes in a calcium ion and phosphate ion containing saturated electrolyte solution. In the Figure, the collagen fibrils are easily recognizable in a branched network. On the surfaces of the fibrils mineralization has taken place at selected sites. The hydroxyapatite (HAP) crystallites are easily recognizable by brighter areas in needle-shaped form. The HAP crystallite formation does not occur evenly (heterotactic) on the collagen fibril surface but at some selected preferred sites.

Figure 1B:
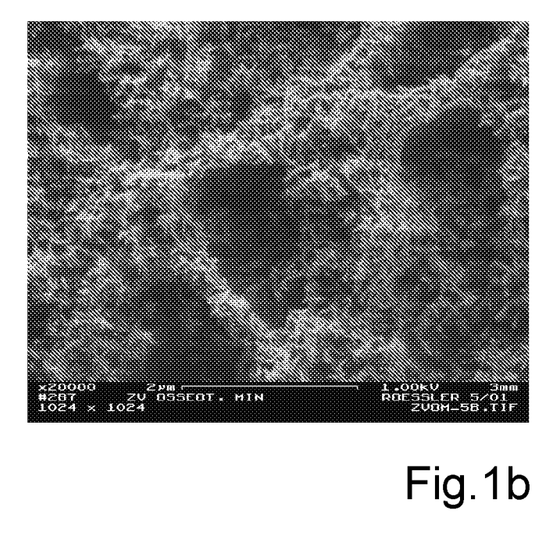

FIG. 1B shows the HAP covering of the surface after an exposure time of two hours. The apatite crystallites have increased in numbers, they penetrate each other mutually and cover the collagen fibrils located underneath irregularly on account of their crystallographic structure.

The growth of the HAP crystallites occurs therefore not epitactically with respect to the collagen surface but heterotactically at individual selected sites of the surface with the crystal appearance that is typical for hydroxyapatite (needle formation). In contrast to living organisms, osteocalcin for nucleus formation is absent so that the mineral formation does not take place in platelet form in the gap regions of the collagen I fibrils. The needle formation is the result of the growth of the crystallites in crystallographically preferred directions. The growth of the needles is interrupted in the preferred direction only when they grow together. The formed crystal surfaces are still capable of growth afterwards. On account of the present surface morphology and surface energy, there is thus growth of other crystal surfaces or formation of new crystallites on the HAP-surface. This fact leads to the formation of a crystal appearance of the hydroxyapatite as it is likewise know from other biological surfaces. These HAP crystals have thus the undesirable property of removing from the electrolyte surroundings calcium as well as phosphate ions causing them to grow and the calcium and phosphate ions to be bound in physiological solutions.

A high bioactivity as it is usually exhibited by unmodified calcium phosphate phases leads, on the one hand, to the formation of an apatite layer which has been positively valued up to now, but then also to the depletion of the surroundings of the biomaterial with respect to calcium ions; this can affect negatively the cells involved in remodeling and thus bone healing or new bone formation. Therefore, one cannot speak of bioactivity in a narrowly defined sense. How high the calcium ion concentration must be in the cell surroundings of osteoblasts or also osteoclasts to create ideal conditions for new bone formation is still unclear up to now and will vary in a wide range. However, it is unambiguously clear that calcium phosphate-based materials are needed whose calcium binding and release behavior can be adjusted in a predetermined way. In this connection, according to the current level of knowledge, metastable calcium phosphate phases, as for example tricalcium phosphate, bruschite, and octacalcium phosphate, are unsuitable because their dissolution behavior is too fast with respect to the bone healing process.

It is therefore the object of the invention to form hydroxyapatites whose growth is inhibited after the nucleus formation and themselves in predetermined way release calcium and phosphate ions after implantation in the bone tissue. The proliferation and the differentiation of bone-forming cells should be influenced positively by this effect and the bone formation should be promoted.

SUMMARY OF THE INVENTION

According to the invention, the object is solved by growth-inhibited hydroxyapatite which is contained in agglomerates of prestructured collagen templates on which epitactic hydroxyapatite crystallites with a crystallite size below their critical nucleus radius are formed. The diameter of the prestructured collagen templates amounts to 1.5-100 nm, preferably 1.5- to 10 nm.

The growth-inhibited hydroxyapatite (in the following referred to as wHAP) according to the invention is present in the form of wHAP containing agglomerates. The wHAP agglomerates are generally smaller than 1 μm and have preferably a size of 400 to 600 nm. The wHAP crystallites that have grown on the prestructured collagen templates have a crystallite size of 0.5 to 20 nm, preferably from 1 to 10 nm, particularly preferred from 1 to 5 nm. In the agglomerate the prestructured collagen templates with the wHAP crystallites grown thereon enclose each other or are agglomerated. The prestructured collagen templates on which the wHAP crystallites epitactically have grown or formed are referred to in the following as structural building blocks.

The growth-inhibited hydroxyapatite according to the invention (in the following also referred to as wHAP) is in a metastable state, is unstable in physiological electrolyte solutions and is dissolved thereby. Physiological electrolyte solutions are characterized in that the ion concentrations (e.g., sodium, chloride) and the osmolarity correspond to that of the human serum.

The HAP crystallites according to the invention dissolve in a narrow range of calcium concentration of 2.2 to 2.7 mmol/l. The proliferation and the differentiation of bone-forming cells are positively influenced by the additional supply of calcium ions in the vicinity of a bone defect, and bone formation I bone healing is promoted.

Because the metastable state is caused by a kinetic inhibition of the crystal growth, it is referred to as growth-inhibited hydroxyapatite. It differs from the customary one by a three-dimensional (spatial) specific inhibition of the growth process of the HAP crystallites, and this is achieved in the third dimension by thickness growth as well as by a selfassembly process of the structural building blocks. In the two-dimensional plane, the nucleus formation and the growth of the HAP crystallites are controlled on account of the specific preparation process such that a planar, homogeneous, nanocrystalline structure is produced with crystallite sizes that are below the critical nucleus radius of HAP.

The effect of the growth inhibition is achieved in that the wHAP crystallite size is limited with the aid of the prestructured collagen template below a critical nucleus radius.

The critical nucleus radius r* is calculated with a simplified approach of a spherical nucleus to $$r^* = 2\gamma/\Delta g_V - \Delta g_E)$$

Herein $\Delta g_V$ means the specific free volumetric enthalpy of the HAP and $\Delta g_E$ means the specific elastic distortion energy of the HAP crystallites and $\gamma$ the interface energy. Moreover, the following applies $$\Delta g_V = (H_S/c_s)(c_s - c)$$

Herein is $H_S$: the melting enthalpy for HAP,
$c_s$: the saturation concentration for Ca ions and phosphate ions
c: the actual concentration With epitactic growth, $\Delta g_E$ reaches values of about 0.01 and can therefore be neglected.

Therefore, the bigger the critical nucleus radius, the higher the interface energy. The interface energy depends, on the one hand, on the geometry of the surface and, on the other hand, on the size of the crystallites as well as the portion of internal interfaces (crystal boundaries). In case of nanocrystallinity, the interface energy considerably increases when the crystallite size is smaller than 10 nm. This value is obtained also in the calculation of the critical nucleus radius for hydroxyapatite in physiological solutions.

The equation of the specific free volumetric enthalpy $\Delta g_V$ also takes into account the oversaturation $\Delta c = c_s - c$. The greater the oversaturation, the smaller the critical nucleus radius. The proportion of $\Delta g_E$ is very low in case of epitactic growth on surfaces of biopolymers.

Crystallite sizes of wHAP below 10 nm are reached in a defined way when HAP crystallites grow epitactically on the prestructured collagen templates. An agglomerate is created with a HAP structure which is, on account of the nanocrystallinity as well as the selfassembly, far removed from thermodynamic balance.

In the third dimension, the growth of the HAP crystallites is restrained by agglomerate formation of the structural building blocks. The structural building blocks, the prestructured collagen templates on which wHAP crystallites are formed, exhibit the astonishing property that they are capable of assembling themselves. This is possible only when the structural components are capable of diffusion or migration. In the course of this process, the structural building blocks under formation of HAP/HAP-contacts agglomerate and form a spherical agglomerate structure in the micrometer range, and this inhibits further growth of the epitactically grown hydroxyapatite in the third dimension. An optimum is reached when the structural building blocks form spheres/hollow spheres. Other spherical agglomerates however form also, depending on the composition of the electrolyte solution and the electrolyte movement/temperature or diffusion/migration of the involved ions.

The walls of these hollow spheres represent a diffusion barrier for the exchange of Ca ions and phosphate ions. When inside a hollow sphere Ca ions and phosphate ions are used up by growth of existing HAP crystallites, the enclosed electrolyte solution is depleted in Ca ions and phosphate ions. As a result of this reaction, undersaturated electrolyte concentrations result which stop further growth of HAP crystallites. Therefore, the electrolyte concentration is regulated also in terms of an inhibition of the HAP crystal growth due to the selfassembly of the building blocks and the resulting architecture of the structure. The selfassembly thus also entails a self-regulation.

Selfassembly of the macromolecules happens also when they are covered after pre-structuring only partially with hydroxyapatite. In addition to HAP/HAP contacts, also organic/organic as well as mixed ones are possible. Depending on the elasticity of the organic molecules, deviations from the spherical shape occur under these conditions.

In this context, the prestructured collagen templates are selected from prestructured, denatured collagen, prestructured collagen molecules, as for example tropocollagen, prestructured collagen microfibrils, prestructured collagen fibrils, prestructured collagen analogs and/or prestructured collagen fragments and/or prestructured collagen derivatives, as for example gelatin.

The collagen templates that are prestructured by denaturing and/or with sugars or non-collagen proteins are not longer than 1 μm, preferably 50 to 500 nm, and in solutions or gels are capable of diffusion or migration. The diameter of the prestructured collagen template amounts to 1.5-100 nm, preferably 1.5- to 10 nm. The prestructured collagen template control, on the one hand, the nucleus formation and the nucleus growth of the wHAPs as well as, on the other hand, the agglomeration of the prestructured and mineralized collagen templates.

The collagens of the prestructured collagen templates can be recombinant collagen, collagen from Eumetazoa (i.e. true tissue animals, among them Cnidaria and Bilateria), sponge collagens of the classes Demospongia (demosponges) or Calcarea (calcarean sponges), a synthetic collagen analog, a collagen derivative as for example gelatin or a mixture of the above.

Collagen analogs are synthetically produced polypeptide chains whose primary sequence is so designed that they can simulate certain properties of the native collagen monomers.

Recombinant collagens are those whose primary sequence is identical with that of collagen type I. They are produced with the aid of genetically manipulated micro-organisms and are post-treated, if necessary.

Collagen derivatives are compounds which can be formally derived from the basic compound collagen and can be produced from it.

Collagen derivatives are compounds which can be formally derived from the basic compound collagen and can be produced from it such as for example gelatin.

As a collagen template any denatured collagen can be used, i.e. partially or completely (irreversible) denatured collagen and any type (e.g., type I, II, III, IV, V, VI, VII, VIII, IX, X, XI, XII, XIII, XIV, XV, XVI, XVII, XVIII, XIX, XX, XXI, XXII, XXIII, XXIV, XXV, XXVI).

The collagen template can be a solution or a hydrogel.

The collagen templates are denatured or broken up such that their fibrillogenesis is inhibited and the collagen templates are capable of diffusion or migration in solution or in the hydrogel. The length of the collagen templates amounts to less than 1 μm, preferably 50 to 500 nm. The diameter of the prestructured collagen templates amounts to 1.5-100 nm, preferably 1.5-10 nm.

The collagen templates are characterized by pre-structuring of their surfaces. It can be present naturally or can be generated in a predetermined way. This is achieved by sugar molecules or non-collagen proteins. As a sugar mono and disaccharides, glycoproteins, proteoglycans and glycosaminoglycans are suitable. As non-collagen proteins osteocalcin, osteonectin, and osteopontin can be used.

Pre-structuring in the context of the invention is to be understood such that the prestructured collagen templates are functionalized such that hydroxyapatite can grow on their surface which is growth-inhibited on account of the size, pre-structuring and diffusion and migration capability of the prestructured collagen templates. The functionalization can be of natural origin or can be imparted by pre-structuring with sugar molecules or non-collagen proteins.

According to an advantageous embodiment of the invention, the growth-inhibited hydroxyapatite is contained in agglomerates of gelatin molecules on which epitactic HAP crystallites with a crystallite size below their critical nucleus radius are formed, wherein the gelatin molecules have a diameter between 1.5 and 20 nm, preferably 10 to 15 nm, and the HAP crystallites have a crystallite size of 1 to 5 nm.

These gelatin molecules have a high surface energy in comparison to their volume. For this reason, they are particularly suited for crystallite formations with comparably small specific volumetric enthalpy. On account of their high surface energy in comparison to the volumetric enthalpy, these gelatin molecules are capable of selfassembly in solutions or gels. They minimize their surface energy in that they combine with other gelatin molecules to spherical agglomerates.

The structural building blocks formed in this manner, having an average length of about 300 nm, agglomerate to hollow spheres. These are referred to as spherical wHAP agglomerates of a size smaller than 1 μm, preferably 400 to 600 nm.

The growth-inhibited hydroxyapatite according to the invention differs from apatites used already up to now by the fact that in physiological solutions it does not bind, but releases, calcium and phosphate ions. Thereby they promote bone formation and bone growth in a detectable extent.

According to the invention the growth-inhibited hydroxyapatite is produced with the following steps:
a) mineralization of prestructured collagen templates in supersaturated solutions containing Ca ions and phosphate ions, wherein the prestructured collagen templates are capable of diffusion or migration, so that epitactic HAP crystallites grow on the collagen templates and the collagen templates with grown-on HAP crystallites agglomerate on account of their diffusion or migration capability.
b) separation of the agglomerates.

Prestructured, denatured collagen, prestructured collagen molecules, as for example tropocollagen, prestructured collagen microfibrils, prestructured collagen fibrils, prestructured collagen analogs and/or prestructured collagen fragments and/or prestructured collagen derivatives, as for example gelatin, are used as prestructured collagen templates.

The collagens of the prestructured collagen templates can be recombinant collagen, collagen from Eumetazoa (i.e. true tissue animals, among them Cnidaria and Bilateria), sponge collagen of the classes Demospongia (demosponges) or Calcarea (calcarean sponges), a synthetic collagen analog, a collagen derivative as for example gelatin or a mixture of the above.

The collagen templates used according to the invention are denatured or broken up such that their fibrillogenesis is inhibited but the collagen templates are capable of diffusion or migration in solution or in the hydrogel. The length of the prestructured collagen templates amounts to preferably 50 to 500 nm.

The prestructured collagen templates used according to the invention are characterized by the pre-structuring of their surfaces. It can be present naturally or can be generated in a predetermined way. This is achieved by sugar molecules or non-collagen proteins. As a sugar mono and disaccharides, glycoproteins, proteoglycans and glycosaminoglycans are suitable. As non-collagen proteins osteocalcin, osteonectin, and osteopontin can be used.

Pre-structuring in the context of the invention is to be understood such that the prestructured collagen templates are functionalized such that hydroxyapatite can grow on their surface which is growth-inhibited on account of the size, pre-structuring and diffusion and migration capability of the prestructured collagen templates. The functionalization can be of natural origin or can be imparted by pre-structuring with sugar molecules or non-collagen proteins.

The mineralization of the prestructured collagen templates occurs either without current at different pH values in supersaturated solutions which contain the prestructured collagen template in desired concentration in addition to calcium and phosphate ions. The ion concentrations of the solutions are selected such that a Ca/P ratio of about 1.67 is adjusted.

Furthermore, the mineralization can be carried out in calcium and phosphate electrolyte solutions with addition of organic compounds by applying an electric field (e.g., potentiostat, galvanostat) from the exterior.

It is possible also to carry out the mineralization in partial steps beginning with incubation in a calcium ion containing solution. The calcium ions then deposit in a predetermined way on the prestructured template surfaces. Only then in a second mineralization step, the deposition of HAP is initiated by incubation of the collagen templates in a phosphate-containing solution. The calcium ions, beforehand bound within the gel, thereby determine quite decisively the growth inhibition. The reverse order is not conducive to achieving the goal. These processes can be controlled additionally through external electric fields.

A further advantageous mineralization resides in that the mineralization steps are separated spatially: The calcium-containing or the phosphate-containing solutions are arranged spatially in such a way relative to the template gel that only by ion diffusion in the gel, i.e. in the presence of the prestructured template, a mineralization occurs. This process can be controlled through external electric fields.

The preparation of the wHAP agglomerates can also be realized in that the calcium and phosphate ion-containing initial solutions are diffusing into a collagen hydrogel that has been prestructured beforehand, preferably consisting of gelatin, and in the gel wHAP crystallites are formed which agglomerate to wHAP agglomerates.

On account of the mobility of the prestructured collagen templates and their ability to mutually assemble or agglomerate, calcium nuclei and as a result HAP crystallite nuclei are formed only to a limited extent on the surfaces of the collagen template. As a result, growth-inhibited hydroxyapatites with dimensions of 1 to 5 nm are obtained which agglomerate to spherical agglomerates with average diameters in a two-digit nanometer range. When the formation of the calcium phosphate phases occurs in absence of e.g. collagen molecules or with a greatly disturbed interaction with the collagen molecules, needle-shaped or platelet-shaped crystals within the micrometer range are generated in general.

The so formed wHAP agglomerates can be separated by removing the excess template. This can be done, for example, by temperature increase, acid treatment and enzyme treatment.

According to the method according to the invention, agglomerates are obtained in the form of powders/particles that contain superfine-grain, nanocrystalline wHAP crystallites of a crystal size of approx. 0.5-20 nm preferably 1-20 nm, particularly preferred 0.5-5 nm, especially preferred 1-5 nm.

The growth-inhibited HAP is generated according to an advantageous embodiment of the method according to the invention on surfaces of gelatin molecules which are not capable anymore of fibrillogenesis as a result of the preparation process. Growth-inhibited HAP forms on gelatin molecules whose diameters are between 1.5 and 20 nm, preferably between 10 to 15 nm. Under these boundary conditions, structures with HAP crystallites form on the molecule surface whose average linear grain size is not greater than 1 to 5 nm.

The constitution of the wHAP agglomerates and the wHAP crystallites affects the solution precipitation behavior in contact with natural or simulated body fluids in that unmodified bioactive HAP crystallites grow with calcium and phosphate absorption, while the wHAP crystallites covered with collagen templates on the other hand do not absorb ions from the surroundings and can be dissolved instead.

Growth-inhibited HAP crystallites according to the invention are biocompatible.

In the process of pre-structuring, the collagen template changes its morphology by interaction with the abovementioned substances. Along with this, the charge conditions change and thereby the primary to ternary structure of the template as well as the arrangement of the prestructured template components (quarternary structure) relative to each other.

Depending on pre-structuring of the collagen template, superfine-grain wHAP crystallites with dimensions generally of 1 to 5 nm are produced on the template surfaces in the mineralization process. On account of the selected preparation conditions, a quasi single crystal formation is prevented. With the goal of minimizing the surface energy, the wHAP crystallites form wHAP agglomerates (=composite particles) with dimensions of typically 500 nm with quasi-amorphous shape (for energetic reasons roughly spherical) and the abovementioned property profile.

The growth-inhibited HAP crystallites can be incorporated as a mineral component into other, preferably organic, materials. The property of calcium and phosphate release can thereby be imparted to these materials. Moreover, the degradation properties of the HAP crystallites can be adjusted. The strength of the composite increases as the proportion of the nanophases increases.

Composite materials obtained in this way can be used in biomedicine as an implant material which is required to exhibit a release of calcium and phosphate ions in addition to having biocompatibility, degradability and sufficient strength.

The growth-inhibited hydroxyapatite according to the invention can be used for coating implant materials.

BRIEF DESCRIPTION OF THE DRAWINGS

With the aid of enclosed illustrations and embodiments the invention will be explained in more detail. In this context it is shown in.

DESCRIPTION OF PREFERRED EMBODIMENTS

Dissolvable collagen I (Vitrogen 100 (purified collagen) in 0.012 N HCl; 3 mg/ml, Cohesion, Palo Alto, USA) is available ready-to-use.

Low molecular weight chitosan (Sigma) is dissolved in 0.01 N HCl so that a stock solution of a concentration of 2 mg/ml is provided.

A buffer solution (1.52 mg/ml $KH_2PO_4$, 7.12 mg $Na_2HPO_4$, 0.63 mg/ml NaCl in deionized water) is produced.

Collagen solution and chitosan solution are mixed in a volumetric ratio of 2:3. This corresponds to a mass ratio of 1:1. This mixture is mixed in a volumetric ratio of 1:1 with the buffer solution, The batch reacts at 37° C. for a period of 24 hrs. Prestructured collagen molecules are obtained. After centrifugation (10,000 rotations/minute, 15 minutes, at 21° C.) the prestructured collagen fibrils are introduced into gelatin heated to 50° C. (10 mg/ml). Typical concentrations of the collagen are between 2.5-25 m-%.

The template batch prepared in this way is layered at 4° C. into a vessel and is gelled so that the vessel is divided into two sections approximately of the same size. In a first partial step the template gel is incubated in a calcium ion containing solution. Calcium ions are thereby adhered in a predetermined way on the prestructured template surfaces. Only in a second step the mineralization is initiated by incubation of the gel in a phosphate-containing solution. The ion concentrations of the solutions are chosen such that a Ca/P ratio of about 1.67 is adjusted. The calcium ions bound beforehand in the gel thereby determine quite decisively the later growth inhibition. The reverse order is not conducive to achieving the goal.

In a particularly preferred variant a spatial separation of the mineralization step occurs: The calcium-containing or the phosphate-containing solutions are arranged spatially relative to the template gel such that only by ion diffusion in the gel, i.e. in the presence of the prestructured template, a mineralization can occur. This process can be controlled through external electric fields.

Figure 2:
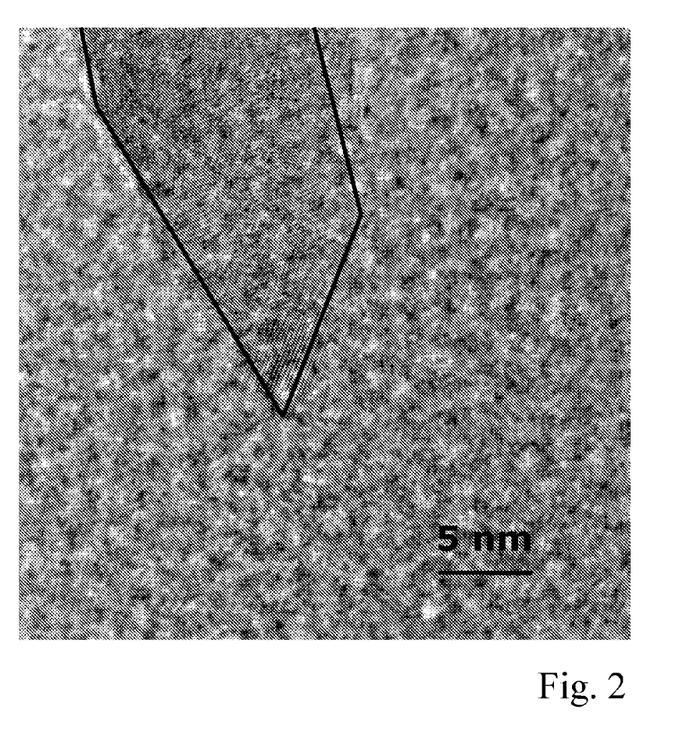

FIG. 2 shows a maximum-resolution transmission electron microscope image of a prestructured collagen molecule with epitactically deposited wHAP crystallites. The radius of the molecule amounts to about 7 nm and the average linear crystallite grain size is between 1 and 5 nm. The generation of this image was only possible by transmission electron microscopy on a carbon net. The amorphous carbon appears in the image in the form of different shades of gray. In order to make the collagen molecule in the image more clearly visible, it was roughly delimited with yellow lines. One recognizes within the boundary individual areas which are distinguished by a parallel striation of lines. These are the net planes of wHAP crystallites. Whether the whole surface is covered with HAP crystallites cannot be unambiguously answered based on this image. Hence, the claim to partial covering.

Figure 3:
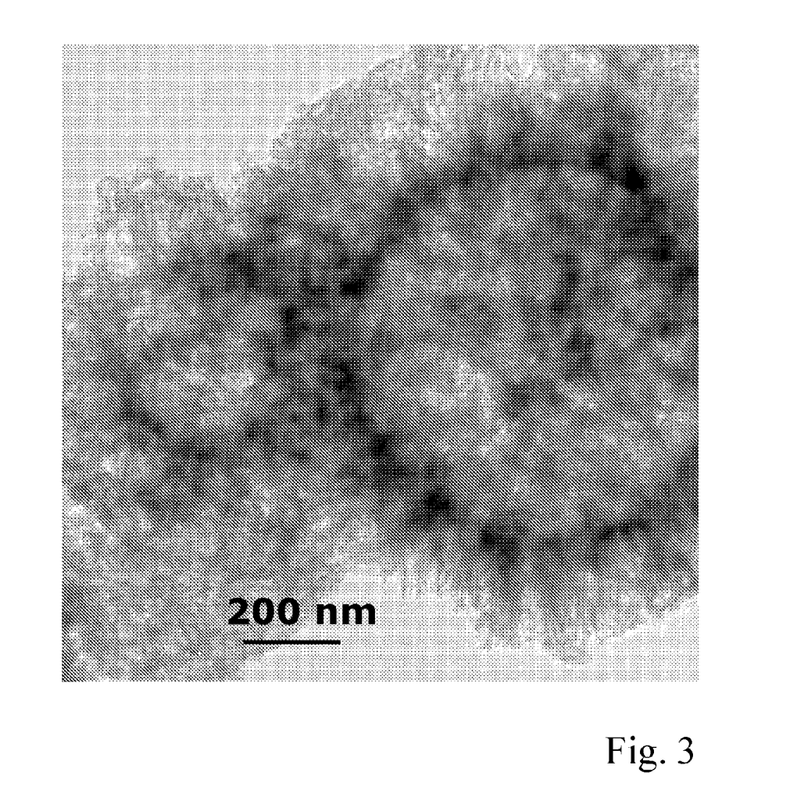

FIG. 3 shows a high-resolution transmission electron microscope image which illustrates the configuration of two spherical wHAP agglomerates. It can be seen that they are hollow spheres. The elements shown enlarged in FIG. 2 are selfassembling in that they adjoin each other in parallel in accordance with their longitudinal axes and thus form the agglomerates.

Calcium and phosphate ions diffuse in all cases for a period of time of up to 4 weeks into the template gel and cause mineralization of the prestructured templates. By the free three-dimensional mobility of all involved particles (ions and template) the prestructured and mineralized template molecules align mutually in such a way that an unhindered crystal growth is prevented. Instead, the growth-inhibited composite particles agglomerate with the goal of minimization of the surface energy.

The growth-inhibited composite particles formed in the template gel can be separated by removing the excess template, This can be done, for example, by temperature increase, acid treatment and enzyme treatment. In the preferred case the composite agglomerates (=wHAP) are separated after heating to 50° C. and centrifugation for 10 minutes at 5,000 g and dried afterwards.

Figure 4:
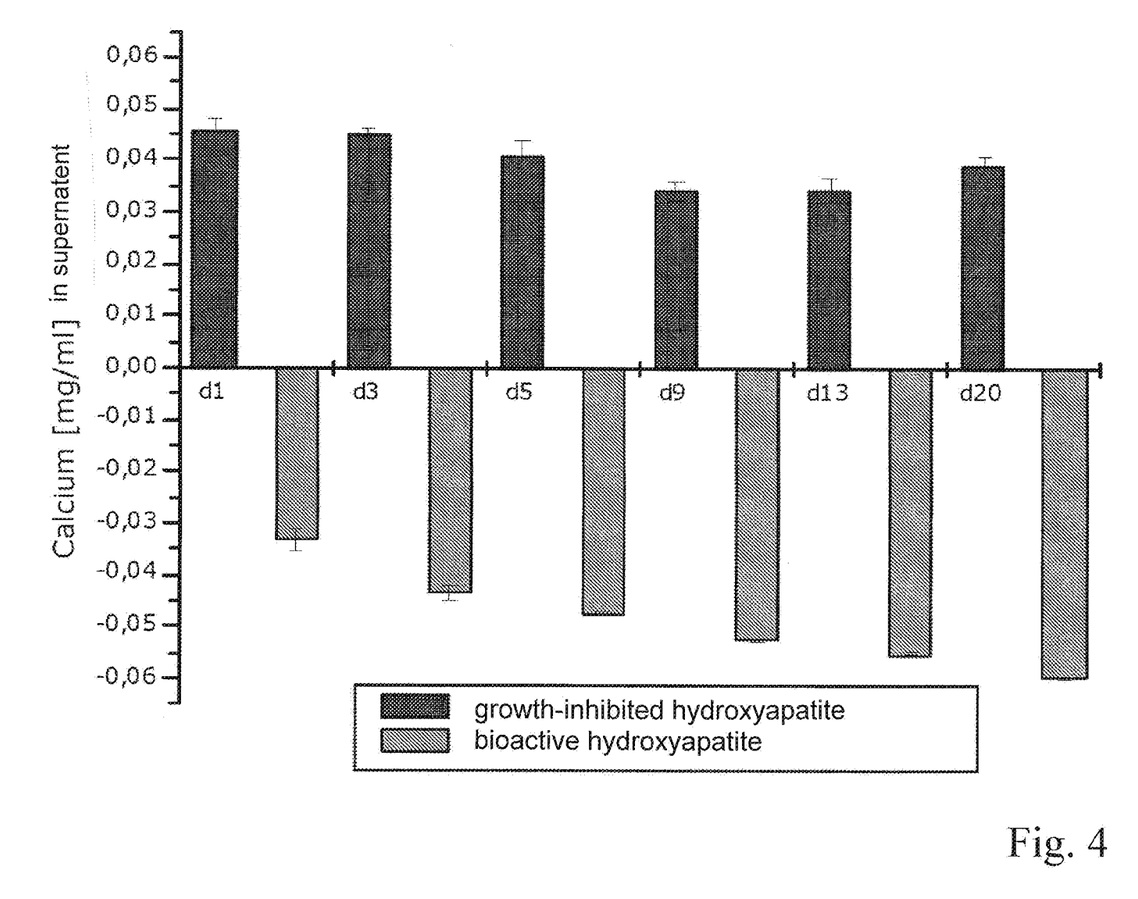

The solution/precipitation behavior of conventional bioactive HAP and growth-inhibited HAP (wHAP) produced according to the described method was examined and shown in the diagram of FIG. 4. For its generation in each case same masses of the bioactive HAP and wHAP were incubated in 2 ml of a simulated body fluid at 37° C. and the calcium concentration in the supernatent measured for a period of 20 days. In the o-cresolphthalein complex method applied here, calcium reacts in alkaline solution with o-cresolphthalein with formation of a violet dye complex whose intensity is proportional to the calcium concentration in the sample.

For the test, 10 μl of sample solution each was transferred to microtiter plates. Afterwards, 300 μl each of the measuring reagent, obtained by mixing in a ratio of 1:1 the reagents 1 (AMP buffer, pH 10.7) and 2 (o-cresolphthalein complex, 8-hydroxyquinoline, HCl, detergent) contained in the calcium kit, were added by pipette. After 10 minutes of mixing on a shaker the absorption of the resulting dye was measured at 570 nm. A calibration line was generated with the aid of a dilution series of the calcium standard contained in the kit (2.5 mmol).

The negative values determined for the bioactive HAP characterize the absorption of calcium from the solution and growth of the mineral phase. By contrast, the positive values determined for wHAP characterize that it releases calcium into the solution and therefore does not grow.

What is claimed is:

1. A method for preparing growth-inhibited hydroxyapatite with the steps
providing prestructured collagen templates that are denatured or broken up so that fibrillogenesis of the prestructured collagen templates is inhibited, wherein the prestructured collagen templates are capable of diffusion or migration;
mineralizing the prestructured collagen templates by;
incubating in a first step the prestructured collagen templates in supersaturated solutions containing Ca ions, wherein the Ca ions deposit in a predetermined way on the prestructured collagen templates, and
subsequently incubating in a second step the prestructured collagen templates in a phosphate-containing solution to grow epitactic hydroxyapatite crystallites on the prestructured collagen templates, wherein the Ca ions deposited in the first step determine decisively growth inhibition of the hydroxyapatite crystallites,
agglomerating the prestructured collagen templates with grown-on hydroxyapatite crystallites by diffusion or migration of the prestructured collagen templates,
separating the agglomerates.

2. The method according to claim 1, wherein prestructured, denatured collagen, prestructured collagen molecules, prestructured collagen microfibrils, prestructured collagen analogs, prestructured collagen derivatives and/or prestructured collagen fragments with a length of <500 nm and a diameter of 1.5 nm to 20 nm are used as the prestructured collagen templates.

3. The method according to claim 1, wherein the prestructured collagen templates are prestructured with sugar molecules and/or non-collagen proteins.

4. The method according to claim 1, wherein mineralizing is done without current or electrochemically.

* * * * *